(12) United States Patent
Quintanilla Almagro et al.

(10) Patent No.: US 6,706,293 B1
(45) Date of Patent: Mar. 16, 2004

(54) PHARMACEUTICAL COMPOSITION CAPABLE OF REGULATING THE EXPRESSION OF ADHESION MOLECULES

(75) Inventors: Eliseo Quintanilla Almagro, Ali (ES); Joaquín Diaz Alperi, Ali (ES)

(73) Assignee: Especialidades Farmaceuticas Centrum, S.A., Alicante (ES)

( * ) Notice: Subject to any disclaimer, the term of this patent is extended or adjusted under 35 U.S.C. 154(b) by 0 days.

(21) Appl. No.: 09/889,846

(22) PCT Filed: Jan. 21, 2000

(86) PCT No.: PCT/ES00/00026

§ 371 (c)(1),
(2), (4) Date: Jun. 10, 2002

(87) PCT Pub. No.: WO00/43023

PCT Pub. Date: Jul. 27, 2000

(30) Foreign Application Priority Data

Jan. 25, 1999 (SE) .............................................. 9900182

(51) Int. Cl.[7] .............................................. A61K 35/78
(52) U.S. Cl. ........................................ 424/763; 424/773
(58) Field of Search ................................. 424/763, 773

(56) References Cited

U.S. PATENT DOCUMENTS 5,601,829 A * 2/1997 Quintanilla Almagro et al.

FOREIGN PATENT DOCUMENTS

EP 0503208 9/1992
WO WO 9807432 2/1998

OTHER PUBLICATIONS

Sempere et al. Immunology (Dec. 1999), vol. 98, suppl. 1, pp. 105.*
Bernd et al, *Arzneimittel–Forshung*, 45(8):901–904 (1995).
Sempere et al, *Br. J. Clin. Pharmacol.*, 43(1):85–89 (1997).
Rayward et al, *Int. J. Immunopharmacol.*, 19(1):9–14 (1997).

* cited by examiner

*Primary Examiner*—Leon B. Lankford, Jr.
*Assistant Examiner*—Susan D Coe
(74) *Attorney, Agent, or Firm*—Sughrue Mion, PLLC

(57) ABSTRACT

Pharmaceutical composition with adhesion molecule expression regulating activity.

The invention relates to a novel pharmaceutical application of a pharmaceutical composition exhibiting regulating activity of the expression of adhesion molecules integrins, selectins and immunoglobulins and its application as anti-inflammatory agent. Said pharmaceutical composition contains Anapsos, a water-soluble extract and a lipo-soluble extract of the rhizomes of *Polypodium leucotomos* as active substance in addition to acceptable excipients.

4 Claims, No Drawings

PHARMACEUTICAL COMPOSITION CAPABLE OF REGULATING THE EXPRESSION OF ADHESION MOLECULES

This application is a 371 of PCT/ES00/00026, filed Jan. 21, 2000.

FIELD OF THE INVENTION

The present invention relates to a novel pharmacological use of Anapsos. Anapsos is a neutral extract of Polypodium comprising 118 milligrams of a water soluble extracts and 2 milligrams of a lipid soluble fraction.

The present invention describes the involvement of the Anapsos in the regulation of the expression of the adhesion molecules. Anapsos reduces the expression of the alpha chain of integrins β-2 (CD11a and CD11b), the beta chain of integrins β-2 (CD18), and the differentiation antigen CD54 of the immunoglobulins superfamily. It is also capable of normalizing alterations of the immunological phenotype.

Further, is described the use of Anapsos in any diseases where an excess of inflammation, derived from cellular and tissue lesions, is responsible for pathologically symptoms and indications.

BACKGROUND OF THE INVENTION

The cells of the immune system are in contact with other cells and the extra-cellular matrix in order to efficiently perform their required functions. This is due to that they must be able to recognize the situation of their surroundings. Accordingly, the leukocytes not only have specific surface receptors capable of being specifically activated in response to determined stimuli, but also comprises a number of molecules which globally are called adhesion molecules. The adhesion molecules act as receptors for ligands which are situated on other cells and as receptors capable of binding amino acid sequences present in different extracellular matrix proteins, such as collagen, fibronectin, lamina, and others. The adhesion molecules, beside being involved in the cell—cell and cell—extracellular matrix adhesion, collaborate in the cellular activation by sending co-activator signals into the interior of the cell.

The migration of leukocytes to the tissue, essential for the immunological response, is mediated by a number of molecular interactions where the adhesion molecules play a fundamental role. The adhesion molecules are classified into 3 structural based categories:

the selectins the family of integrins the superfamily of immunoglobulins

In the first step of inflammation, the leukocytes acumulate around the endothelial wall causing the endothelial cells to remove themselves from each other. This initial process is mediated by the interaction of specific endothelial selecting (selectin E and P) and their corresponding leukocyte receptor (sLex) and between leukocyte selectin L and specific adhesion molecules of the endothelium. Simultaneously, with the expression of the adhesion molecules, are also released pro-inflammatory cytokines. Following, an activation signal induces a conformational change in the extra-cellular domains of the leukocyte integrins which gives a stronger adhesion. This is mediated by interactions between specific integrins and their ligands (LFA-1/ICAM-1, VLA-4/VCAM-1). As a consequence of the leukocyte/endothilium adhesion the accumulation of leukocytes is reduced and there are produced extravasation and migration of the leukocytes, from the blood circulation to the focus of inflammation, by chemotaxis. Consequently, the adhesion molecules are responsible for different processes of adhesion, mediating the final adhesion to the endothelium, the extravasation, and the migration towards the focus of inflammation.

The alpha and beta Chains of the integrins β-2 (CD11a, CD11b, CD18) are extended throughout all tissues. Consequently, a decrease in their expression gives an anti-inflammatory effect in the tissues. The adhesion molecule CD54 belongs to the immunoglobulin superfamily and is also highly distributed in various tissues, such as endothelium, leukocytes, etc.

In patients with multiple sclerosis there has been observed an increase in the lymphocyte population CD4+CD29+CD45RA. Further, recent data from the literature of virgin and memory cells indicates that revertant CD4+CD29+CD45RA+ cells are of fundamental importance as these are the authentic memory cells. They have a longer half-life as compared to CD45RO+ and once activated capable of being maintained years in the organism.

Inflammation, which might well be a normal physiological process, is when it is taken to its extreme converted into a pathological issue. For example, this happens in the major part of the auto-immune processes (systematic or organ specific), chronic inflammatory diseases, or infections which symptoms are characterized by an exaggerated inflammation giving rise to the corresponding damage of organs or tissues. Consequently, any medicament capable of decreasing the expression of the adhesion molecules, which under inflammation processes normally have an increased expression, may be suitable for the treatment of these diseases, independently if the aetiological cause of the specific disease. Such disease might be neuro-degenerative disorders (multiple sclerosis, Alzheimer), and connective tissue diseases (systematic lupus eritematose, Sjögren syndrome, reumatoide arthritis, Behcet disease, etc).

The anti-inflammatory action, due to reduction of the expression of the adhesion molecules, is performed independently of the inhibition-stimulation of the inflammatory cytokines and the stimulatory effect of the cellular immunity (increase of TH1-like cytokines and increase of T CD8+ lymphocytes and NK cells).

The extracts of the genus of the Polypodiaceae family have traditionally been used in Central America in the popular medicine attributing to it different activities such as: anti-inflammatory activity, Boletin de la Sociedad Quimica del Perú pag 91 (1988); prevention of tumor malignant, Nature 214: 1256–1258 (1967). There have been described clinical effects in diseases related to immunological deficits, such as atopic dermatitis; Dermatológica 173: 154–156 (1986); atopic dermatitis, Allergology et Inmunopathology 15: 185–189 (1987); International Journal of Dermatology 13: 276–282 (1974); Planta Médica 58: 306–310 (1992) and vitiligo, International journal of Dermatology 28: 479 (1989). In these publications it has been identified that the extracts of Polypodium leucotomos have activity in relation to hyperqueratosis, paraquerotosis, epidermal mitosis, and lesions of the epidermis.

The extracts of these ferns have been described to have immuno-modulatory capacity in patients with atopic dermatitis, giving a normalization of the CD4+/CD8+ relation after treatment with extract of Polypodium leucotomos (Anapsos®), Dermatólogica 173:154–56 (1986); Annals Inmulogie 134:393–400 (1983). Annals of Psychiatry 3: 329–341 (1992) describes that the Anapsos® improve the memorizing, Decrease the levels of cytokines IL-1β-2 and IL-2 in the frontparietal cortex and decrease IL-1β in hypocampus, Br. J. Clin. Pharmacol 43: 85–89 (1997) describes the immuno-modulatory effect in vitro of the polar extract of *Polypodium leucotomos* (Anapsos®) in relation to the cytokines IL-1β, IL-2, IL-10, INF-(which could give a pleiotropic effect in the different populations of the immune system.

Concerning the patent literature following documents of relevance have been identified.

The European patent application EP-503.208 describes a process for obtaining a water-soluble extract by extraction of the leaves and/or rhizomes of different ferns. This document specifies that these extracts have immunological activity and consequently useable in diseases involving a depression of the immune system, generally with a deficit of T suppressor lymphocytes, and with beneficial affects in the auto-immuno diseases and viral infections. Examples of pathological utilities are: reumatoide arthritis, lupus eritematose, syndrome of Sjögren, multiple sclerosis, hepatitis B, syndrome of Di George, auto-haemolytic anaemia, atopic dermatitis, psoriasis, Basedow disease, Chron disease, mistenia, vitiigo, herpes zoster, etc. The extract increases the level of T-suppressor lymphocytes.

The Spanish patent ES-2.088.770 teaches a pharmaceutical composition based on a water-soluble and a lipid soluble fraction of the leaves and/or rhizomes of different ferns with beneficial effects against cognitive dysfunctions, and/or neuroimmunes, in particular for the treatment of Alzheimer disease.

The U.S. Pat. No. 5,614,197 describes the use of extracts of Polypodium as photo-protector agents and as antioxidants. The Spanish patent ES-470.204 relates to natural terpenes with anti-psoriasis activity which are obtained by extraction of the rhizomes and leaves of different ferns. The Spanish patent ES-490.293 relates to a medicament with anti-inflammatory effects in pathological problems which affects the osteolocomotor apparatus of the human organism, specially the arthritis. The medicament is obtained as extracts from fern of the family Polypodiaceae using both the leaves and the rhizomes. The U.S. Pat. No. 3,839,553 uses the extracts of Polypodium as capillary conditioners. The French patent FR-2.395.266 relates to obtaining a a-d-gluco-octane-delta-l-lactone-eno-diol and its calcium salt starting from the ferns of Polypodium, having immuno-suppressing and antiviral activity in mammalians.

The patent application having the publication number WO-97/40838 describes the use of a sulfur lipid for the treatment of inflammatory disorders of the skin, specially in psoriasis, by inhibition of the plaque aggregation factor. The sulfur lipid is obtained from leaves by methanol extraction.

The Polypodium extracts as described in the art are water-soluble or hydrophilic extracts which may be obtained by extraction with polar solvents followed by different purification steps such as purification by resins via interchancing of ions, absorption over active carbon followed by evaporation of the solvents or lyophilization. Corresponding, the lipid or lipid soluble fractions may be obtained by extraction with apolar solvents such as hexane, chloroform, or ether to obtain the different triterpenes present in the leaves and/or rhizomes. The pharmaceutical composition of the present invention comprises as active ingredient the extract of Polypodium, Anapsos, corresponding to the pharmaceutical composition as described in the Spanish patent ES-2.088.770. It comprises a water-soluble and a lipid soluble fraction and pharmaceutically acceptable carries. Each unit dose consist of 120 mg extracts, wherein 118 mg is a water-soluble fraction, equivalent to 60 mg of alcohol extract, and 2 mg is a lipid soluble fraction.

Suitable excipients are the ones as normally used in the pharmaceutical industry such as a lactose preparation, starch, magnesium stearate, silicium dioxide. It may be possible to use other excipients and in other proportions.

The water-soluble extract is obtained by maceration, in water for 24–48 hours, the leaves and rhizomes of the ferns of *Polypodium aureum, Polypodium leucotomos, Polypodium vulgare, Polypodium trisereiale, Polypodium aquilinum, Drypteris crassirhizoma*, or *Cyathe taiwamiana*. The extract is characterized by the presence of quinine acid, malic acid, lactic acid, citric acid, fumaric acid and by the absence of any kind of sulfur lipid. The lipid soluble fraction is characterized by the presence of Neo-hop-13(18)-eno, Fern-9-(11)-eno, and Hop-(22)-29-eno as identified via mass spectrometry.

The documents of the prior art describe different activities, sometimes in an empirical manner without specifying the mechanism, of the polar and apolar extracts of the rhizomes and/or leaves of the ferns of the Polypodiaceae family.

The pharmacologically actions may be summarized as:

Immuno-modulatory activity in diseases with a deficit in T-suppressor lymphocytes, infectious and autoimmunes, where the extracts exhibit an pleiotropic effect over the different populations of cytokines, Collagenpoyetic activity and application in psoriasis, atopic dermatitis, Anti-inflammatory activity of the osteolocomotor apparatus, principally the arthritis, Anti-inflammatory activity characterized by the inhibition of the plaque aggregation factor.

In none of the identified prior art documents it has been described that the extracts of the different ferns are capable of regulating the expression of the adhesion molecules nor that these are capable of regulating the lymphocyte CD4+CD29+CD45RA+ populations present in increased amounts in patients with multiple sclerosis.

SUMMARY OF THE INVENTION

The problem to be solved by the present invention is to provide a novel therapeutic application of the Anapsos based on the regulation of the different cellular mediators. The regulation of the expression of the adhesion molecules (the decrease of the expression of the chains of integrins and the immunoglobulin superfamily) and the normalization of the lymphocyte CD4+CD29+CD45RA+ population makes the Anapsos a medicament suitable for treatment of diseases which relate to an inflammatory process, in particular in the treatment of multiple sclerosis.

DETAILED DESCRIPTION OF THE INVENTION

The present inventors have demonstrated, that the Anapsos (118 mg of a water-soluble extract and 2 mg of a lipid soluble fraction of Polypodium) has regulatory effects in relation to the expression of adhesion molecules, in mononuclear cells of the peripheral blood of healthy humans, both in vivo and in vitro. Further, it has been demonstrated that Anapsos has a capacity similar to azathioprine to recover the normality of the lymphocyte CD4+CD29+CD45RA+ population, present in increased amounts in patients with multiple sclerosis, thereby obtaining a stabilization of the patients.

At a dose from 0 to 5000 µg/ml of Anapsos and using different doses of phytohaemagglutinin, the Anapsos in vitro is capable of inhibiting the increase of the expression of the adhesion molecules (CD54 and CD11b), as induced by the phytohaemagglutinin, in studies realized on mononuclear cells of human peripheral blood. The results are most significant at a dose of 150 µg/ml of Anapsos and 10 µg/ml of phytohaemagglutinin.

After administration of 720 mg of extract per day for 11 days in a human, the Anapsos decreases the percentage of the lymphocyte populations CD11a, CD11b, and CD54. Accordingly, the extract inhibits the expression of certain adhesion molecules of the integrins $\beta 2$ (CD11a, CD11b) and of the superfamily of immunoglobulins (CD54).

Accordingly, beside the stimulating action on the cellular immunity as performed by the cytokines and its immunomodulatory action as described in the art, the Anapsos has a strong anti-inflammatory capacity, similar to phenylbutazone, used as a control in anti-inflammatory studies in rats. The anti-inflammatory effects of Anapsos has not been directly related to its capacity of regulating the expression of the adhesion molecules.

A pharmaceutical composition based on water-soluble and lipid soluble extracts of Polypodium has, in clinical studies performed on humans, been demonstrated to be effective against some diseases which involve inflammatory processes such as multiple sclerosis, prostatitis, and pharyngitis. Between them, these diseases have a different aetiological cause.

Below, the invention is described by way of examples. These are not limiting on the scope of the invention.

EXAMPLES

Example 1

Study of the Anti-inflammatory Capacity

| Materials: |
| --- |
| Female WISTAR rats of 150 ± 15 g |
| Pletismometer LETICA |
| Weight METTLER AJ 100 |
| Weight COBOS D 600 |
| Phenylbutazone |
| DIFCO |
| CMC and Tween 80 |

Method:

A study of the anti-inflammatory activity has been made in acute and chronic phase in rats. The method used was as described by Mizushima. The reference medicament (Phenylbutizene, dose 80 mg/Kg) and the products of the study (dose equivalent to 1.25 g extract per kg weight of animal) were dissolved in a solution of 1% of CMC (carboxymethylcellulose) in distilled water (w/v) and Tween 80: distilled water (0.2:3.3-v/v), in order to be administrated orally.

Six days after inoculation, by intradermal route of 0.1 mL of the complete adjuvant Freund (DIFCO) in the basal part of the tail, was injected 0.1 mL of a suspension of carrageenin type IV 2% (w/v) at the aponeurosis of the left back foot.

The volume of the foot of the animal was measured, using a water pletismometer, immediately before the carrageenin injection (basal volume) and afterwards at 3, 5, and 7 hours (acute phase of the inflammation) and at 24, 48, 72, and 96 hours (chronic phase of inflammation).

The products of the study, the phenylbutazone, and the carrier were administrated, orally and in portions of 6 animals, 1 hour before the carrageenin injection and at 24, 48 and 72 hours.

Results:

The percentage of inhibition of the inflammation was calculated by comparing the increase of the volume of the animal foot in respect of its basal volume, for each group of animals and in relation to the control group. The control group was given the carrier of phenylbutazone and the products of the study. The statistical significance was evaluated via the T Student test. The results are shown below.

| % INHIBITION OF THE INFLAMMATION | | | | | | | |
| --- | --- | --- | --- | --- | --- | --- | --- |
| | 3 h | 5 h | 7 h | 24 h | 48 h | 72 h | 96 h |
| Control | — | — | — | — | — | — | — |
| Phenylbutazone | 41% | 27% | 21% | 36% | 60% | 56% | 40% |
| Anapsos | 29% | 35% | 41% | 43% | 50% | 54% | 48% |

The results show that the Polypodium extract exhibits an inhibitory activity on the inflammation, superior to the control in the acute phase and similar to phenylbutazone in the acute phase.

Example 2

Clinical Studies of the Effect of Anapsos Against Different Pathologies

Multiple sclerosis: Patients with multiple sclerosis were over 1 year provided with a treatment of 720 mg extract/day. The result was that the for the disease most characteristic alterations of the immunological phenotype were corrected giving a clinical stabilization of the patients. Further, the lymphocyte CD4+CD29+CD45RA+ population was normalized.

Prostatitis: Three days treatment with a dose of 240 mg extract, 60 minutes before the principal dinners, gave an improvement of the patients and all symptoms disappeared.

Pharyngitis: A dose of 120 mg extract gave favorable effects in the problems of pharyngitis, in particular for pharyngitis in its subacute period.

Example 3

In Vitro Study of the Adhesion Molecules In Peripheral Blood Mono-nuclear Cells (PBMNc).

Peripheral blood was extracted from 10 healthy individuals and the mononuclear cells was separated via Fycoll-Hypaque density gradient centrifugation. The cells was cultivated in plane bottom microtiter plates, at a titer of 1 million/ml for 48 hours in a $CO_2$ incubator, with phytohaemagglutinin (PHA) at concentrations of 0, 0.5, 2, 5 and 10 µg/ml and/or with Anapsos at concentrations between 0 to 5000 µg/ml.

Finalized the culturing, the lymphocytes was analyzed by flow cytometry. The expression of determined adhesion molecules (CD11a, CD11b, CD18, CD54) was studied in relation to the different conditions of stimuli. En parallel to the culture as described above, a culture for 5 days was made under the same conditions of stimuli as above. Tritium thymidine was added 16 hours before finalizing the culture. Terminated the culture, the cells was washed with the Harvester and flashing liquid was incorporated into the cells. The cellular incorporation of tritium thymidine was measured via a β counter. During the culturing, the cells were photographed via an inverted microscope. The results are shown below.

Expression, in vitro, of different adhesion molecules of peripheral blood mononuclear cells.

| N = 10 | CD11a | CD11b | CD18 | CD54 |
|---|---|---|---|---|
| PHA10 | 22% | 35% | 27% | 9% |
| ANP 150 | 15% | 14% | 19% | 0% |
| PHA + ANP | 16% | 23% | 25% | 3% |
| CONTROL | 17% | 20% | 20% | 2% |

Example 4

Expression In Vivo of the Adhesion Molecules In Peripheral Blood Mono-nuclear Cells (PBMNc).

10 voluntary persons took for 11 consecutive days 720 mg/day of Anapsos. Peripheral blood was extracted from all of those persons the day before starting the treatment, the day after, at four days, and after the final administration. The mononuclear cells was separated via Fycoll-Hypaque density gradient centrifugation and the different lymphocyte populations were analyzed with respect of the differentiation markers CD11a and CD11b. The results are shown below.

Expression, in vitro, of different adhesion molecules of peripheral blood mononuclear cells.

| N = 10 | PRE | 24H | 72H | 96H | RETIRED |
|---|---|---|---|---|---|
| CD11b | 13% | 4% | 2% | 1% | 12% |
| CD11a | 14% | 6% | 3% | 1% | 15% |

What is claimed is:

1. A method for normalization of C4+CD29+CD45RA+ lymphocyte populations comprising administering, to a subject afflicted with a disease wherein said populations are increased, a pharmaceutically effective amount of a composition comprising a water-soluble fraction from rhizomes of Polypodium and a lipid-soluble fraction from rhizomes of Polypodium; and a pharmaceutically acceptable carrier.

2. The method of claim 1, wherein said composition comprises 118 mg of said water-soluble fraction and 2 mg of said lipid-soluble fraction.

3. A method for treatment of multiple sclerosis comprising administering, to a subject afflicted with multiple sclerosis, a pharmaceutically effective amount of a composition comprising a water-soluble fraction from rhizomes of Polpodium and a lipid-soluble fraction from rhizomes of Polypodium; and a pharmaceutically acceptable carrier.

4. The method of claim 3, wherein said composition comprises 118 mg of said water-soluble fraction and 2 mg of said lipid-soluble fraction.

* * * * *